US007087608B2

(12) United States Patent
Atkins et al.

(10) Patent No.: US 7,087,608 B2
(45) Date of Patent: Aug. 8, 2006

(54) USE OF PDGF RECEPTOR TYROSINE KINASE INHIBITORS FOR THE TREATMENT OF DIABETIC NEPHROPATHY

(76) Inventors: Robert Charles Atkins, 7 Wentworth Avenue, Canterbury, Victoria 3126 (AU); Steven James Chadban, 73 Ardoyne Street, Blackrock, Victoria 3193 (AU); Mark Emmanuel Cooper, 60 Chatsworth Road, East Prahran, Victoria 3181 (AU); Richard Ernest Gilbert, 16 Mary Street, West St. Kilda, Victoria 3182 (AU); Prudence Ann Hill, 7 Wentworth Avenue, Canterbury, Victoria 3126 (AU); Darren James Kelly, 1 Commerford Place, Chirnside Village, Victoria 3116 (AU); David John Nikolic-Paterson, 170 Mt Grantview Road, Pearcedale, Victoria 3912 (AU)

( * ) Notice: Subject to any disclaimer, the term of this patent is extended or adjusted under 35 U.S.C. 154(b) by 449 days.

(21) Appl. No.: 10/220,214

(22) PCT Filed: Jan. 3, 2001

(86) PCT No.: PCT/EP01/02340

§ 371 (c)(1),
(2), (4) Date: Apr. 15, 2003

(87) PCT Pub. No.: WO01/64200

PCT Pub. Date: Sep. 7, 2001

(65) Prior Publication Data

US 2003/0186977 A1    Oct. 2, 2003

(30) Foreign Application Priority Data

Mar. 3, 2000    (EP) .................................. 00810181

(51) Int. Cl.
*A61K 31/497*    (2006.01)
*A61K 31/505*    (2006.01)

(52) U.S. Cl. .......................... 514/252.18; 514/252.14; 514/269; 514/272

(58) Field of Classification Search ..................... None
See application file for complete search history.

(56) References Cited

U.S. PATENT DOCUMENTS 5,093,330 A    3/1992    Caravatti et al.

FOREIGN PATENT DOCUMENTS

| EP | 0 564 409 A | 10/1993 |
|----|----|----|
| EP | 0 622 077 | 11/1994 |
| EP | 0 826 686 A | 3/1998 |
| WO | 96 13259 A | 5/1996 |
| WO | 96 33179 | 10/1996 |
| WO | 98 35958 | 8/1998 |
| WO | 99 03854 A | 1/1999 |
| WO | 99 58128 A | 11/1999 |
| WO | 00 09098 A | 2/2000 |

OTHER PUBLICATIONS

Baran, Dana et al., "The new tyrosine kinase inhibitor CGP 53716 specifically inhibits PDGF-driven murine mesangial cell (MC) proliferation," Journal of the American Society of Nephrology, vol. 9, No. Program and Abstr. Issue, pp. 433A (1997).

Bird, Eileen et al., "Effects of a platelet-derived growth factor (PDGF) receptor kinase inhibitor, RPR-101511a, in acute glomerulonephritis in rats," Journal of the American Society of Nephrology, vol. 10, p. 568A (1999).

Woo K. T., "Recent concepts in the pathogenesis and therapy of IgA nephritis," Annals Academy of Medicine Singapore, vol. 25(2), pp. 265-269 (1996).

Gilbert, Richard E. et al., "PDGF signal transduction inhibition ameliorates experimental mesangial proliferative glomerulonephritis," Kidney International, vol. 59(4), pp. 1324-1332 (2001).

(Continued)

*Primary Examiner*—Dwayne Jones
(74) *Attorney, Agent, or Firm*—Oona A. Jackson; George R. Dohmann (57) ABSTRACT

The present invention relates to the use of PDGF receptor tyrosine kinase inhibitors, especially of N-phenyl-2-pyrimidine-amine derivatives of formula (I), in which the symbols and substituents have the meaning as defined herein in free form or in pharmaceutically acceptable salt form, in the manufacture of a pharmaceutical composition for the treatment of diabetic nephropathy; to a method of treatment of warm-blooded animals, including humans, suffering from diabetic nephropathy; and to the use of a PDGF receptor tyrosine kinase inhibitor of the formula (I), wherein $R_1$ is pyridyl bonded at a carbon atom, $R_2$, $R_3$, $R_5$, $R_6$ and $R_8$ are each hydrogen, $R_4$ is lower alkyl, $R_7$ a radical of formula (II): —N($R_9$)—C(=X)—(Y)$_n$—$R_{10}$, wherein $R_9$ hydrogen, X is oxo, n is 0 and $R_{10}$ is 4-methyl-piperazinyl-methyl, or a pharmaceutically acceptable salt thereof for the manufacture of a medicament for treating glomerulonephritis, chronic pyelonephritis or IgA nephropathy.

6 Claims, 4 Drawing Sheets

OTHER PUBLICATIONS

Sugimoto, Yukio et al., "Preparation of N-(hetero)aryl-p-aminophenol derivatives for elimination of active oxygen species," Database Chemabs Online, Chemical Abstracts, Database Accession No. 116:41485.

Chadban et al., "Defective B Cell CD22 Expression by Lupus Prone NZBWF1 Mice," Abstract, Australia and New Zealand Society of Nephrology, Ann. Scientific Meeting, Melbourne, end of Mar. 2000.

Nakamura et al., "mRNA Expression of Growth Factors in Glomeruli from Diabetic Rats," Diabetes, vol. 42, pp. 450-456 (1999).

Throckmorton et al., "PDGF and TGF-β mediate collagen production by mesangial cells exposed to advanced glycosylation end products," Kidney International, vol. 48, pp. 111-117 (1995).

Doi et al., "Receptor-specific increase in extracellular matrix production in mouse mesangial cells by advanced glycosylation end products is mediated via platelet-derived growth factor," Proc. Natl. Acad. Sci. USA, vol. 89, pp. 2873-2877 (1992).

Hulthen et al., "Vascular Hypertrophy and Albumin Permeability in a Rat Model Combining Hypertension and Diabetes Mellitus," American Journal of Hypertension Ltd., pp. 895-901 (1996).

Cao et al., "Angiotensin converting enzyme inhibition and calcium antagonism attenuate streptozotocin-diabetes-associated mesenteric vascular hypertrophy independently of their hypotensive action," Journal of Hypertension, vol. 16, 793-799 (1998).

Allen et al., "Role of Angiotensin II and Bradykinin in Experimental Diabetic Nephropathy," Diabetes, vol. 46, pp. 1612-1618 (1997).

Buchdunger et al., "Selective inhibition of the platelet-derived growth factor signal transduction pathway by a protein-tyrosine kinase inhibitor of the 2-phenylaminopyrimidine class," Proc. Natl. Acad. Sci., vol. 92, pp. 2558-2562 (1995).

Major et al., "Inhibition of Cell Growth: Effects of the Tyrosine Kinase Inhibitor CGP 53716," The Journal of Pharmacology and Eperimental Therapeutics, vol. 283(1), pp. 402-410 (1997).

Remuzzi et al., "Prevention of Renal Injury in Diabetic MWF Rats by Angiotensin II Antagonism," Exp Nephrology, vol. 6, pp. 28-38 (1998).

Woo K. T., "Recent concepts in the pathogenesis and therapy of IgA nephritis," Annals Academy of Medicine Singapore, vol. 25(2), pp. 265-269 (1996).

Gilbert, Richard E. et al., "PDGF signal transduction inhibition ameliorates experimental mesangial proliferative glomerulonephritis," Kidney International, vol. 59(4), pp. 1324-1332 (2001).

Sugimoto, Yukio et al., "Preparation of N-(hetero)aryl-p-aminophenol derivatives for elimination of active oxygen species," Database Chemabs Online, Chemical Abstracts, Database Accession No. 116:41485, 1991.

USE OF PDGF RECEPTOR TYROSINE KINASE INHIBITORS FOR THE TREATMENT OF DIABETIC NEPHROPATHY

The present invention relates to a new use of PDGF receptor tyrosine kinase inhibitors, especially of N-phenyl-2-pyrimidine-amine derivatives of formula I in which the symbols and substituents have the meaning as given hereinafter in free form or in pharmaceutically acceptable salt form, said compound group being referred to hereinafter collectively as COMPOUNDS OF THE INVENTION, in the manufacture of a pharmaceutical composition for the treatment of diabetic nephropathy, and to a method of treatment of warm-blooded animals, including humans, in which a therapeutically effective dose of a COMPOUND OF THE INVENTION is administered to a warm-blooded animal suffering from diabetic nephropathy.

The present invention relates the use of PDGF receptor tyrosine kinase inhibitors for the manufacture of a medicament for treating diabetic nephropathy.

The present invention relates in particular to a new use of N-phenyl-2-pyrimidine-amine derivatives of formula I, wherein $R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl—substituted pyridyl bonded at a ring carbon atom and unsubstituted or substituted at the nitrogen atom by oxygen;

$R_2$ and $R_3$ are each independently of the other hydrogen or lower alkyl;

one or two of the radicals $R_4$, $R_5$, $R_6$, $R_7$ and $R_8$ are each nitro, fluoro-substituted lower alkoxy or a radical of formula II wherein $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic—aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy, or of a salt of such a compound having at least one salt-forming group, for the manufacture of a medicament for treating diabetic nephropathy.

1-Methyl-1H-pyrrolyl is preferably 1-methyl-1H-pyrrol-2-yl or 1-methyl-1H-pyrrol-3-yl.

Amino- or amino-lower alkyl-substituted phenyl $R_1$ wherein the amino group in each case is free, alkylated or acylated is phenyl substituted in any desired position (ortho, meta or para) wherein an alkylated amino group is preferably mono- or di-lower alkylamino, for example dimethylamino, and the lower alkyl moiety of amino-lower alkyl is preferably linear $C_1$–$C_3$alkyl, such as especially methyl or ethyl.

1H-Indolyl bonded at a carbon atom of the five-membered ring is 1H-indol-2-yl or 1H-indol-3-yl.

Unsubstituted or lower alkyl-substituted pyridyl bonded at a ring carbon atom is lower alkyl-substituted or preferably unsubstituted 2-, 4- or preferably 3-pyridyl, for example 3-pyridyl, 2-methyl-3-pyridyl or 4-methyl-3-pyridyl. Pyridyl substituted at the nitrogen atom by oxygen is a radical derived from pyridine N-oxide, i.e. N-oxido-pyridyl.

Fluoro-substituted lower alkoxy is lower alkoxy carrying at least one, but preferably several, fluoro substituents, especially trifluoromethoxy or 1,1,2,2-tetrafluoro-ethoxy.

When X is oxo, thio, imino, N-lower alkyl-imino, hydroximino or O-lower alkyl-hydroximino, the group C=X is, in the above order, a radical C=O, C=S, C=N—H, C=N-lower alkyl, C=N—OH or C=N—O-lower alkyl, respectively. X is preferably oxo.

n is preferably 0, i.e. the group Y is not present.

Y, if present, is preferably the group NH.

The term "lower" within the scope of this text denotes radicals having up to and including, 7, preferably up to and including 4 carbon atoms.

Lower alkyl $R_1$, $R_2$, $R_3$ and $R_9$ is preferably methyl or ethyl.

An aliphatic radical $R_{10}$ having at least 5 carbon atoms preferably has not more than 22 carbon atoms, generally not more than 10 carbon atoms, and is such a substituted or preferably unsubstituted aliphatic hydrocarbon radical, that is to say such a substituted or preferably unsubstituted alkynyl, alkenyl or preferably alkyl radical, such as $C_5$–$C_7$alkyl, for example n-pentyl. An aromatic radical $R_{10}$ has up to 20 carbon atoms and is unsubstituted or substituted, for example in each case unsubstituted or substituted naphthyl, such as especially 2-naphthyl, or preferably phenyl, the substituents preferably being selected from cyano, unsubstituted or hydroxy-, amino- or 4-methyl-piperazinyl-substituted lower alkyl, such as especially methyl, trifluoromethyl, free, etherified or esterified hydroxy, free, alkylated or acylated amino and free or esterified carboxy. In an aromatic-aliphatic radical $R_{10}$ the aromatic moiety is as defined above and the aliphatic moiety is preferably lower alkyl, such as especially $C_1$–$C_2$alkyl, which is substituted or preferably unsubstituted, for example benzyl. A cycloaliphatic radical $R_{10}$ has especially up to 30, more especially up to 20, and most especially up to 10 carbon atoms, is mono- or poly-cyclic and is substituted or preferably unsubstituted, for example such a cycloalkyl radical, especially such a 5- or 6-membered cycloalkyl radical, such as preferably cyclohexyl. In a cycloaliphatic-aliphatic radical $R_{10}$ the cycloaliphatic moiety is as defined above and the aliphatic moiety is preferably lower alkyl, such as especially $C_1$–$C_2$alkyl, which is substituted or preferably unsubstituted. A heterocyclic radical $R_{10}$ contains especially up to 20 carbon atoms and is preferably a saturated or unsaturated monocyclic radical having 5 or 6 ring members and 1–3 hetero atoms which are preferably selected from nitrogen, oxygen and sulfur, especially, for example, thienyl or 2-, 3- or 4-pyridyl, or a bi- or tri-cyclic radical wherein, for example, one or two benzene radicals are annellated (fused) to the mentioned monocyclic radical. In a heterocyclic-aliphatic radical $R_{10}$ the heterocyclic moiety is as defined above and the aliphatic moiety is preferably lower alkyl, such as especially $C_1$–$C_2$alkyl, which is substituted or preferably unsubstituted.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkylamino, such as dimethylamino. Acylated amino is, for example, lower alkanoylamino or benzoylamino.

Esterified carboxy is, for example, lower alkoxycarbonyl, such as methoxycarbonyl A substituted phenyl radical may carry up to 5 substituents, such as fluorine, but especially in the case of relatively large substituents is generally substituted by only from 1 to 3 substituents. Examples of substituted phenyl that may be given special mention are 4-chloro-phenyl, pentafluoro-phenyl, 2-carboxy-phenyl, 2-methoxy-phenyl, 4-fluoro-phenyl, 4-cyano-phenyl, and 4-methyl-phenyl.

Salt-forming groups in a compound of formula I are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

Compounds of formula I having acidic groups, for example a free carboxy group in the radical $R_{10}$, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethyl-piperazine.

Compounds of formula I having both acidic and basic groups can form internal salts.

For the purposes of isolation or purification, as well as in the case of compounds that are used further as intermediates, it is also possible to use pharmaceutically unacceptable salts. Only pharmaceutically acceptable, non-toxic salts are used for therapeutic purposes, however, and those salts are therefore preferred.

Further suitable PDGF receptor tyrosine kinase inhibitors are disclosed in WO 98/35958, especially the compound of Example 62, and U.S. Pat. No. 5,093,330 in each case in particular in the compound claims and the final products of the working examples, the subject-matter of which are hereby incorporated into the present application by reference to these publications.

Diabetic nephropathy is characterized by a persistent albuminuria (>300 mg/24 h or 200 μg/min), which disease can be diagnosed clinically if the following additional criteria are fulfilled: presence of diabetic retinopathy and no clinical or laboratory evidence of kidney or urinary tract disease other than diabetic glomerulosclerosis. Diabetic nephropathy is the commenest cause of endstage renal failure in the Western World.

It can be shown by established test models and especially those test models described herein that the COMPOUNDS OF THE INVENTION or in each case a pharmaceutically acceptable salt thereof, results in a more effective prevention or preferably treatment especially of diabetic nephropathy, but also of glomerulonephritis, chronic pyelonephritis or IgA nephropathy. The person skilled in the pertinent art is fully enabled to select a relevant test model to prove the hereinbefore and hereinafter indicated therapeutic indications and beneficial effects. The pharmacological activity may, for example, be demonstrated in a clinical study or in the test procedure as essentially described hereinafter.

TEST EXAMPLE 1

Antiproteinuric Action in Rats with Subtotally (⅚) Nephrectomy [Focal Glomerulosclerosis Model; T. W. Meyer and H. G. Renake, Am. J. Physiol. 254, F856 (1988)].

Five-week-old male rats are anesthetized by intraperitoneal injection of pentobarbital sodium and ⅔ of the right kidney is removed. One week later, the entire left kidney is removed under similar anesthesia. After two-week breeding, 24-hour urine is collected and the total protein content and albumin content in the urine is determined by the use of A/G-B test (Wako Pure Chemical Co., Ltd.). On the basis of urinary protein and blood pressure the rats are divided into two groups (vehicle-treated rats and rats treated with 1 mg/kg/day, p.o. of a COMPOUND OF THE INVENTION). Rats undergoing nephrectomy of the left kidney alone are also used as sham operated rats. The COMPOUND OF THE INVENTION is suspended in gum-arabic and the suspension is orally administered once a day for eight week. At the 2nd, 4th, 6th and 8th week of the treatment, 24-hour urine is collected for the determination of urinary total protein and urinary albumin.

TEST EXAMPLE 2

Antiproteinuric Action in Rats with Non-Insulin-Dependent (NIDD) Diabetes (Wistar Fatty Rats) [H. Ikeda et al., Diabetes 30, 1045 (1981)]

On the basis of blood glucose level and urinary protein content, 11-week-old Wistar fatty rats are divided into two groups (vehicle-treated rats and rats treated with 1 mg/kg/day, p.o. of a COMPOUND OF THE INVENTION. Non-diabetic control rats (lean rats) are also used. A COMPOUND OF THE INVENTION is suspended in gum-arabic and the suspension is orally administered once a day for ten days. At the 2nd, 4th, 6th and 8th week of the treatment, 24-hour urine is collected. The urine is centrifuged at 3,000 rpm and a portion of the supernatant is desalted on a column (Pharmacia PD10). Urinary total protein content and albumin content are determined by Lowry and ELISA methods, respectively.

Cellular proliferation and extracellular matrix accumulation are characteristic features of progressive glomerular diseases in man and a major cause of endstage renal failure

TEST EXAMPLE 3

Inhibition of Mesangial Cell Proliferation In Vitro

Interleukin-10 has been shown to stimulate mesangial cell proliferation both in vitro and in vivo (S. J. Chadban, et al. *Lab. Invest.* 76(5, 1997, 619–627). Proliferation of the 1097 rat mesangial cell line (Y. Kakizaki, et al., Clin. Exp. Immunol. 85(1), 1991, 157–63) is assessed by 3H-thymidine uptake. Cells are used between the 30–40$^{th}$ passage. Cells are cultured in RPMI 1640 Medium (Gibco, USA) with heat-inactivated fetal calf serum (FCS), 20 mM HEPES buffer, 100 U/ml penicillin and 100 μg/ml streptomycin in humidified 5% $CO_2$ atmosphere at 37° C. Mesangial cells are plated out at low density in 96-well flat-bottomed microtitre plates in RPMI/10% FCS and allowed to adhere overnight. The subconfluent cells are then starved for 3 days in RPMI/0.5% FCS. The media is then replaced by a solution containing 2 μmol/ml of a COMPOUND OF THE INVENTION, prepared freshly by dissolving the COMPOUND OF THE INVENTION in DMSO and diluting this stock solution 1:10 in normal saline, or control, plus or minus cytokines (R&D systems). Cells are cultured for a further 48 hours and pulsed with 3H-thymidine for 6 hours prior to harvesting. IL-10 (20–100 ng/ml) is added to selected wells. Duplicates of 6 wells are used in all tests and the tests are repeated 3–5 times. It is observed that IL-10 consistently promotes 1097 proliferation, as compared to control (25–75% increase, P<0.01–0.001 vs control). If N-{5-[4-(4-methyl-piperazino-methyl)-benzoylamido]-2-methylpheny}-4-(3-pyridyl)-2-pyrimidine-amine (CGP 57148B) is used as the COMPOUND OF THE INVENTION, this increase in proliferation is completely inhibited by the addition of the COMPOUND OF THE INVENTION.

TEST EXAMPLE 4

Mesangial proliferative Glomerulonephritis induced in Male Wistar Rats with monoclonal OX-7, anti-rat Thy-1.1 Antibody Monoclonal OX-7, anti-rat Thy-1.1 antibody is used for the induction of mesangial proliferative glomerulonephritis (D. W. Mason and A. F. Williams, Biochem. J. 187(1), 1980, 1–20), macrophages are detected using ED1, anti-rat CD68 (C. D. Dijkstra et al., Immunology 54(3), 1985, 589–99) myofibroblasts are identified by labelling with 1A4, anti-human a smooth muscle actin (Sigma Immunochemicals, St. Louis, Mo.) and M744, anti-BrdU (Dako, Glostrup, Denmark) is used to identify proliferating cells. A polyclonal goat anti-bovine/anti-human type IV collagen antibody (Southern Biotechnology, Birmingham, Ala.) is used to examine extracellular matrix.

Anti-Thy-1 nephritis is induced in two groups of 8 male Wistar rats (150–170 g) by i.v. injection of 5 mg/kg OX-7 IgG (D. J. Nikolic-Paterson et al., J. Am. Soc. Nephrol. 7(7), 1996, 1006–14). Starting one day after OX-7 IgG administration, animals receive daily i.p. injections with either CGP 57148B (50 mg/kg) or vehicle control (10% DMSO in saline) until killed on day 6.3 hours prior to sacrifice, all rats are given an i.p. injection of 50 mg/kg bromodeoxyuridine (BrdU) in order to label cells in the DNA synthetic (S) phase of the cell cycle. A group of 8 normal rats are also injected with BrdU 3 hours before sacrifice.

Twenty-four hour urine collections and blood samples are taken on days-3 (prior to test) and day 6. Urinary protein concentration is measured by the benzethonium chloride method (Iwata, J. et al., Clin. Chem. 25(7), 1979, 1317–9). Serum and urine creatinine levels are measured using the Jaffé rate reaction (Larsen, K., Clin. Chim. Acta 41, 1972, 209–17).

Tissues are fixed in 4% neutral buffered-formalin and embedded in paraffin. Kidney sections (4 μm) are stained with periodic-acid Schiff's reagent (PAS). Quantitation of nuclei is performed by examining 50 hilar glomeruli per animal.

Immunostaining is performed as described by Rumble et al., J. Clin. Invest. 99, 1997, 1016–1027. Double immuno-histochemical staining is performed in formalin fixed tissue sections using a microwave-based technique to prevent antibody cross-reactivity (G. H. Tesch, et al, Am. J. Pathol. 151(1), 1997, 141–50).

Sections stained with either BrdU or ED1 antibody are scored for ED1+ or BrdU+. Counting is undertaken using a graticule to measure glomerular tuft area and confined to the glomerular tuft thereby omitting cells within the capillary lumen. Fifty glomeruli are scored for each animal and labelled cells expressed as the mean±SD per $mm^2$. In addition, the number of cells in double-labelled sections are also scored as ED1+BrdU+, ED1+BrdU– and ED1–BrdU+. As podocytes do not proliferate and glomerular endothelial account for <3% of proliferating cells in this disease model proliferating cells are identified as either macrophages ED1+ BrdU+ or proliferating mesangial cells as ED1–BrdU+.

The magnitude of immunostaining for type IV collagen is quantified using computer assisted image analysis as previously described (H. A. Lehr et al., J. Histochem. Cytochem. 45(11), 1997, 1559–65).

Proteinuria is mildly increased in animals that receive OX-7 IgG compared with control rats and is unaffected by CGP 57148B4 treatment (normal control: 2.1±0.2 mg/24 hours; vehicle-treated Thy-1 nephritis: 13.4±7.2 mg/24 hours, CGP 57148B-treated Thy-1 nephritis: 16.4±7.0 mg/24 hours). In PAS-stained sections mesangial hypercellularity and increased mesangial matrix are noted in glomeruli of untreated rats. These pathological changes are not observed in rats receiving CGP 57148B.

Figure 1:
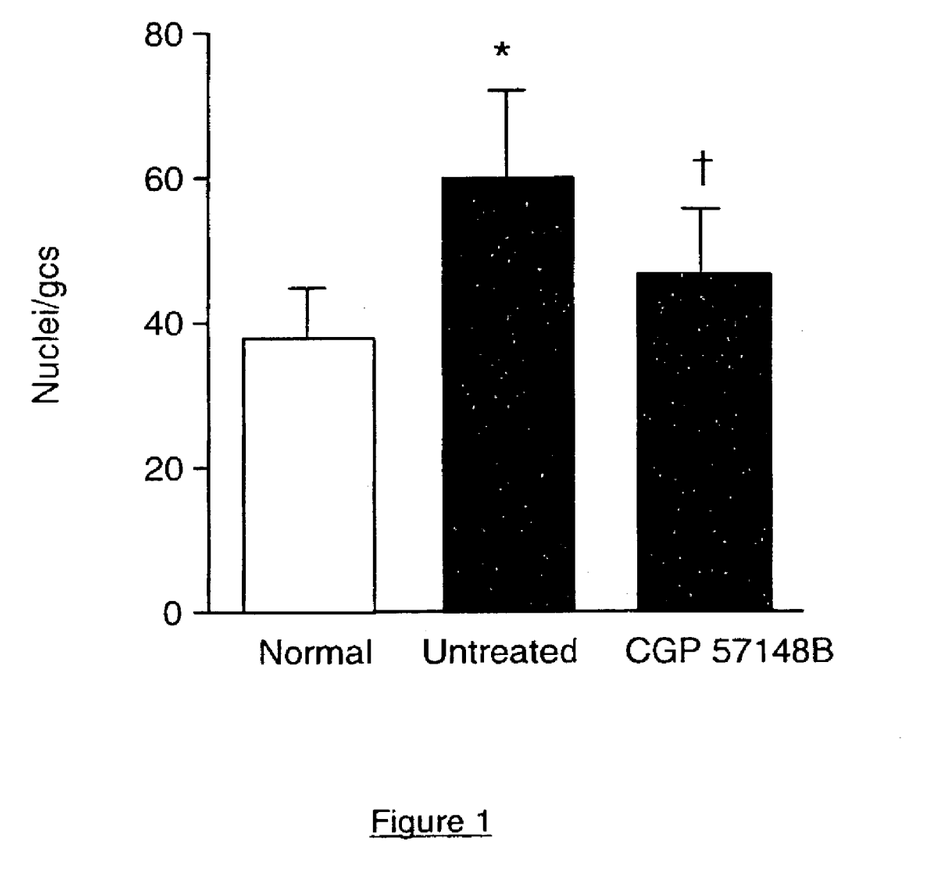
FIG. 1: Glomerular cellularity as assessed by the number of nuclei (mean±SD) per glomerular cross section (gcs) in 50 hilar glomeruli per animal. Glomerular hypercellularity is significantly attenuated by CGP 57148B. *$p<0.05$.
Figure 2:
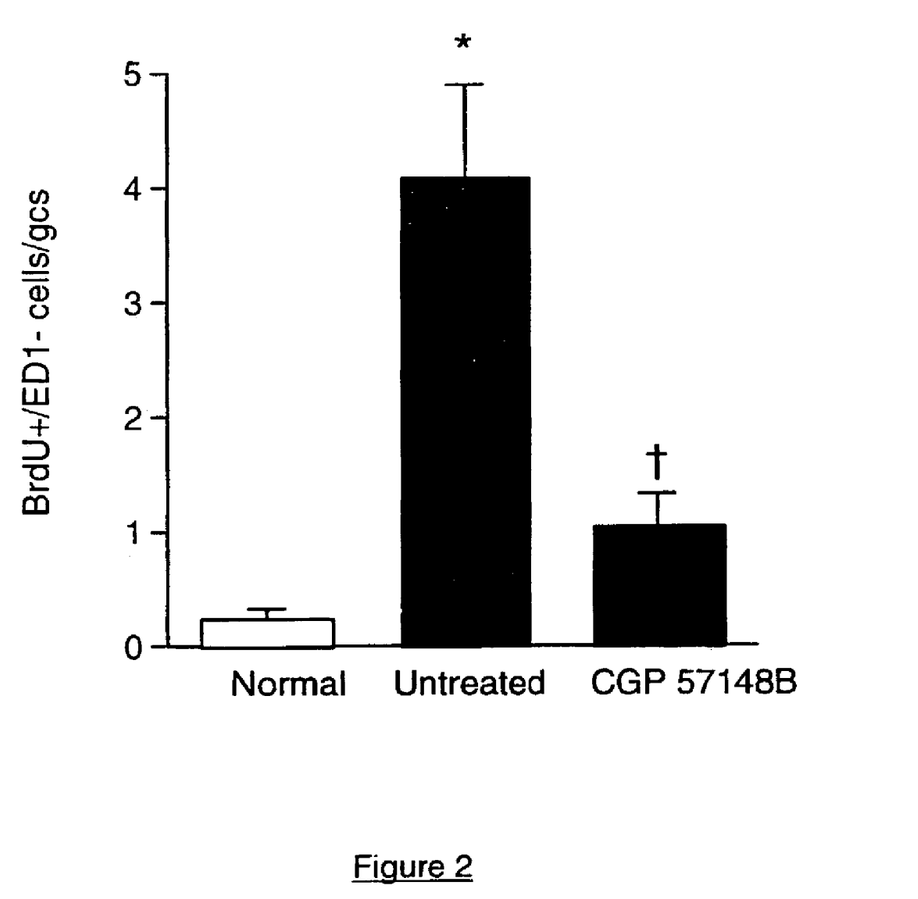
FIG. 2: Mesangial cell proliferation as assessed by the number of BrdU+/ED1-cells (mean±SEM) per glomerular cross section (gcs) in 50 hilar glomeruli per animal. Mesangial cell proliferation is significantly attenuated by CGP 57148B. *$p<0.001$.
Figure 3:
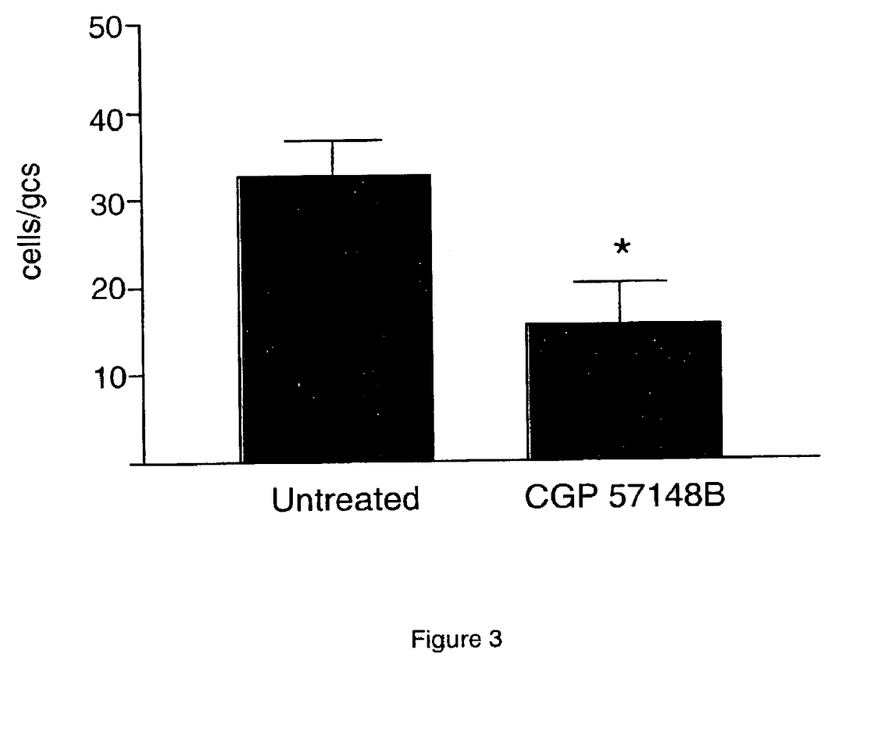
FIG. 3: Activated mesangial cells as assessed by the number of a-smooth muscle actin immunostained cells (mean±SEM) per glomerular cross section (gcs) in 50 hilar glomeruli per animal from untreated and CGP 57148B-treated rats. *$p<0.05$.
Figure 4:
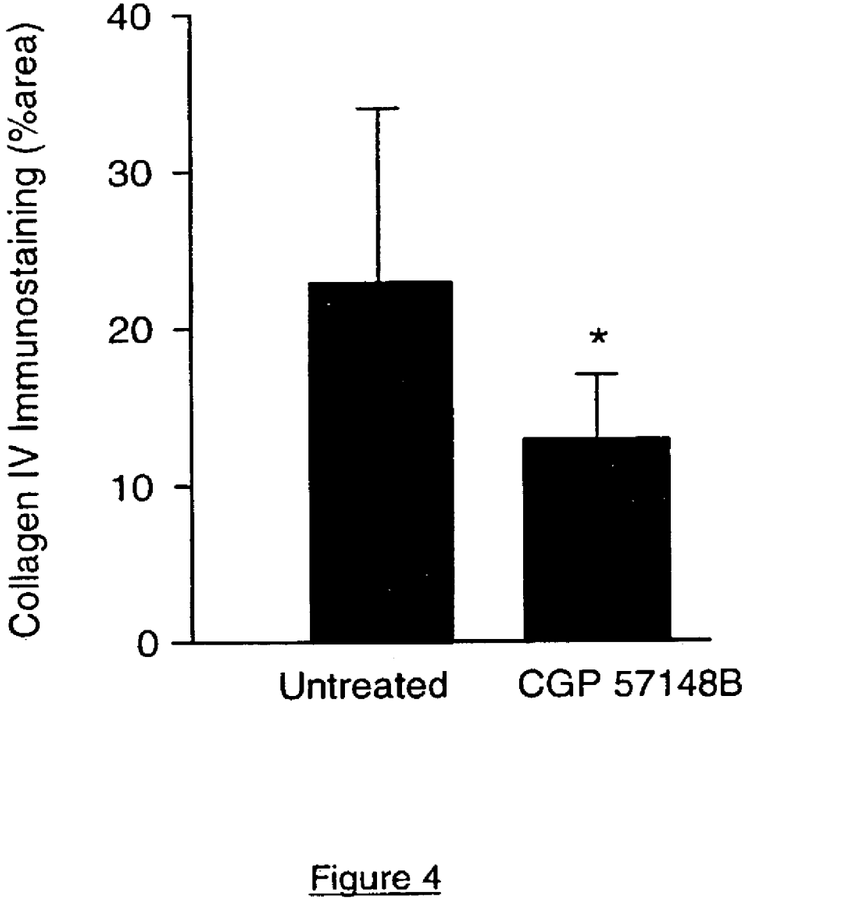
FIG. 4: Quantitation of type IV collagen as assessed by the tractional area (mean±SD) of the glomerulus that is immunostained. *$p<0.05$ versus untreated rats.

Description of the Figures: Animals with anti-Thy-1 nephritis display moderate glomerular hypercellularity when compared with control animals, as assessed by the nuclear counting and is significantly reduced in rats treated with CGP 57148B (FIG. 1). Mesangial cell (BrdU+ED1−) proliferation is increased 5-fold compared with control rats and significantly reduced by treatment with CGP 57148B (FIG. 2). Similarly, the number of activated mesangial cells (a-smooth muscle actin positive) is also increased in untreated rats with anti-Thy-1 nephritis and significantly reduced by the administration of CGP 57148B (FIG. 3). Marked glomerular matrix accumulation of immunostainable type IV collagen is present in untreated rats with anti-Thy-1 nephritis and significantly reduced by the administration of CGP 57148B (FIG. 4).

TEST EXAMPLE 5

Effect of a COMPOUND OF THE INVENTION on Experimental Diabetic Nephropathy in Sprague-Dawley Rats Weighing 200 to 250 g Diabetes is induced in the above rats by injection of streptozotocin (STZ, 55 mg/kg). All animals which develop diabetes within 7 days (random glucose>15 mmol/l) are used for the following test. All diabetic rats receive insulin (human ultralente) 2 units/day to maintain body weight and to avoid ketonuria without euglycaemia leading to glucose levels of 20–25 mM. Control rats are sham injected with buffer alone. A COMPOUND OF THE INVENTION, e.g. CGP 57148B, is administered by gavage at a dose of 20 mg/kg/day. STZ-diabetic rats are randomized to receive the COMPOUND OF THE INVENTION or vehicle. Study groups comprising 16 rats each are as follows: (I) control rats. no drug, (II) control rat, the COMPOUND OF THE INVENTION, (III) STZ-diabetic rat, no drug, (IV) STZ-diabetic rat, the COMPOUND OF THE INVENTION. In weeks 0, 1, 4, 8, 12, 24 and 32 the body weight, blood pressure, glucose, $HbA_{1C}$, water intake and food intake are determined. Histological assessment of the glomeruli and tubulointerstitium are carried out at the end of the study. Glomerular structure is assessed by quantitative electron microscopy histomorphometry. The removed kidneys of the rats are analysed for GBM thickness and fractional mesangial volume.

By the obtained results, e.g. by the amelioration of the pathological findings of mesangial proliferative glomerulonephritis, in particular the amelioration of mesangial hypercellularity and matrix accumulation, it is shown that the COMPOUNDS OF THE INVENTION can be used for the prevention or preferably treatment especially of diabetic nephropathy, but also of glomerulonephritis, chronic pyelonephritis or IgA nephropathy.

Preference is given to COMPOUNDS OF THE INVENTION of formula I wherein one or two of the radicals $R_4$, $R_5$, $R_6$, $R_7$ and $R_8$ are each nitro or a radical of formula II wherein
  $R_9$ is hydrogen or lower alkyl,
  X is oxo, thio, imino, N-lower alkyl-imino, hydroximino or O-lower alkyl-hydroximino,
  Y is oxygen or the group NH,
  n is 0 or 1 and
  $R_{10}$ is an aliphatic radical having at least 5 carbon atoms or an aromatic, aromatic—aliphatic, cycloaliphatic, cycloaliphatic-aliphatic, heterocyclic or heterocyclic-aliphatic radical,
  and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy, and the remaining substituents are as defined above.

Preference is given especially to COMPOUNDS OF THE INVENTION of formula I wherein
  $R_1$ is pyridyl or N-oxido-pyridyl each of which is bonded at a carbon atom,
  $R_2$ and $R_3$ are each hydrogen,
  $R_4$ is hydrogen or lower alkyl,
  $R_5$ is hydrogen, lower alkyl or trifluoromethyl,
  $R_6$ is hydrogen,
  $R_7$ is nitro, fluoro-substituted lower alkoxy or a radical of formula II wherein
    $R_9$ is hydrogen,
    X is oxo,
    n is 0 and
    $R_{10}$ is pyridyl bonded at a carbon atom, phenyl that is unsubstituted or substituted by halogen, cyano, lower alkoxy, carboxy, lower alkyl or by 4-methyl-piperazinyl-methyl, or $C_5$–$C_7$alkyl, thienyl, 2-naphthyl or cyclohexyl, and
  $R_8$ is hydrogen.

Special preference is given to COMPOUNDS OF THE INVENTION of formula I wherein at least one of the radicals $R_4$ and $R_8$ is lower alkyl, and the remaining substituents are as defined above.

Preference is given above all to COMPOUNDS OF THE INVENTION of formula I wherein
  $R_1$ is pyridyl bonded at a carbon atom,
  $R_2$, $R_3$, $R_5$, $R_6$ and $R_8$ are each hydrogen,
  $R_4$ is lower alkyl,
  $R_7$ a radical of formula II wherein
    $R_9$ is hydrogen,
    X is oxo,
    n is 0 and
    $R_{10}$ is 4-methyl-piperazinyl-methyl.

Preference is given above all especially to the COMPOUND OF THE INVENTION of formula I which is CGP 57148B {N-{5-[4-(4-methyl-piperazino-methyl)-benzoylamido]-2-methylphenyl}-4-(3-pyridyl)-2-pyrimidine-amine}.

Very preferably a COMPOUND OF THE INVENTION is used in the form of its monomesylate salt.

The COMPOUNDS OF THE INVENTION of formula I are generically and specifically disclosed in the patent applications EP 0 564 409 A1 and WO 99/03854, in particular in the compound claims and the final products of the working examples, the subject-matter of the final products, the pharmaceutical preparations and the claims are hereby incorporated into the present application by reference to these publications. Comprised are likewise the corresponding stereoisomers as well as the corresponding polymorphs, e.g. crystal modifications, which are disclosed therein.

In EP 0 564 409 A1 the COMPOUNDS OF THE INVENTION of formula I are described to be useful for the therapy of cancer, thrombosis, psoriasis, fibrosis, dermatosclerosis and atherosclerosis. In accordance with the present invention it has now been found that COMPOUNDS OF THE INVENTION surprisingly have a beneficial effect on diabetic nephropathy, glomerulonephritis, chronic pyelonephritis and IgA nephropathy.

In a preferred embodiment of the invention COMPOUNDS OF THE INVENTION are used for the manufacture of a medicament for treating diabetic nephropathy, glomerulonephritis, chronic pyelonephritis or IgA nephropathy, which use is accompanied by the reduction of side effects compared to other medicaments for treating diabetic nephropathy, glomerulonephritis, chronic pyelonephritis or IgA nephropathy which are known in the art.

Preferably, the COMPOUNDS OF THE INVENTION are used for the manufacture of a medicament for the treatment of diabetic nephropathy.

In accordance with the particular findings of the invention, the present invention also provides a method of treatment of warm-blooded animals, including humans, in which an therapeutically effective dose of a COMPOUND OF THE INVENTION is administered to such a warm-blooded animal suffering from glomerulonephritis, chronic pyelonephritis, IgA nephropathy or, preferably, from diabetic nephropathy.

In one preferred embodiment of the invention, the administration of the medicament comprising a COMPOUND OF THE INVENTION effects a reduction of glomerular hypercellularity, of mesangial cell proliferation or of the number of activated mesangial cells, compared to the amount of glomerular hypercellularity, mesangial cell proliferation or the number of activated mesangial cells in a warm blooded animals in one of the test systems described herein or, preferably, in humans suffering from a progressive glomerular disease.

In another preferred embodiment of the invention, the administration of the medicament comprising a COMPOUND OF THE INVENTION effects a reduction of glomerular matrix accumulation of immunostainable type IV collagen compared to the amount of glomerular matrix accumulation in warm blooded animals with an increased glomerular matrix accumulation of immunostainable type IV collagen, in one of the test systems described herein, for example rats with anti-Thy-1 nephritis, or, preferably, in humans suffering from a progressive glomerular disease.

The term "method of treatment" used herein relates especially also to a method of prevention of the diseases mentioned herein, i.e. the prophylactic administration of a pharmaceutical composition comprising a COMPOUND OF THE INVENTION to healthy patients to prevent the outbreak of the diseases mentioned herein, especially diabetic nephropathy.

The present invention relates also to a pharmaceutical composition for the treatment of glomerulonephritis, chronic pyelonephritis, IgA nephropathy or, preferably, of diabetic nephropathy.

Pharmaceutical compositions for the treatment of diabetic nephropathy, glomerulonephritis, chronic pyelonephritis or IgA nephropathy are comprising an effective amount of the COMPOUNDS OF THE INVENTION together with pharmaceutically acceptable carriers that are suitable for topical, enteral, for example oral or rectal, or parenteral administration, and may be inorganic or organic, solid or liquid. For oral administration there are used especially tablets or gelatin capsules comprising the COMPOUNDS OF THE INVENTION together with diluents, for example lactose, dextrose, sucrose, mannitol, sorbitol, cellulose and/or glycerol, and/or lubricants, for example silicic acid, talc, stearic acid or salts thereof, such as magnesium or calcium stearate, and/or polyethylene glycol. Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. The COMPOUNDS OF THE INVENTION can also be used in the form of parenterally administrable compositions or in the form of infusion solutions. Such solutions are preferably isotonic aqueous solutions or suspensions, which, for example in the case of lyophilised compositions that comprise at least one COMPOUND OF THE INVENTION alone or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions which, if desired, may comprise further pharmacologically active substances, such as antibiotics or antidiabetically active compounds, are prepared in a manner known per se, for example by means of conventional mixing, granulating, confectioning, dissolving or lyophilising processes, and comprise approximately from 1% to 100%, especially from approximately 1% to approximately 20%, active ingredient(s).

The COMPOUNDS OF THE INVENTION can, for example, be formulated as disclosed in Examples 4 and 6 of WO 99/03854.

The dosage range of the COMPOUNDS OF THE INVENTION to be employed depends upon factors known to the person skilled in the art including species of the warm-blooded animal, body weight and age, the mode of administration, the particular substance to be employed and the disease to be treated. Unless stated otherwise herein, the COMPOUNDS OF THE INVENTION are preferably administered from one to four times per day. Furthermore, the COMPOUNDS OF THE INVENTION, especially N-{5-[4-(4-methyl-piperazino-methyl)-benzoylamido]-2-methylphenyl}4-(3-pyridyl)-2-pyrimidine-amine (CGP 57148B), are preferably administered to the warm-blooded animal in a dosage in the range of about 1 to 1000 mg, more preferably 50 to 500 mg and most preferably 25 to 250 mg/day, especially when the warm-blooded animal is a human of about 70 kg body weight.

What is claimed is:

1. A method of treating a patient suffering from diabetic nephropathy by administering an effective amount for treating a patient suffering from diabetic nephropathy of 4-(4-methylpiperazin-1-ylmethyl)-N-[4-methyl-3-(4-(pyridin-3-yl)-pyrimidin-2-ylamino)-phenyl]-benzamide, or a pharmaceutically acceptable salt thereof.

2. The method according to claim 1 wherein 4-(4-methylpiperazin-1-ylmethyl)-N-[4-methyl-3-(4-(pyridin-3-yl)-pyrimidin-2-ylamino)-pheny]-benzamide is in the form of its monomesylate salt.

3. A method of treating a patient suffering from glomerulonephritis by administering an effective amount for treating a patient suffering from glomeruloneghritis of 4-(4-methylpiperazin-1-ylmethyl)-N-[4-methyl-3-(4-(pyridin-3-yl)-pyrimidin-2-ylamino)-pheny]-benzamide, or a pharmaceutically acceptable salt thereof.

4. The method according to claim 3 wherein 4-(4-methylpiperazin-1-ylmethyl)-N-[4-methyl-3-(4-(pyridin-3-yl)-pyrimidin-2-ylamino)-pheny]-benzamide is in the form of its monomesylate salt.

5. A method of treating a patient suffering from IgA nephropathy by administering an effective amount for treating a patient suffering from bA nephropathy of 4-(4-methylpiperazin-1-ylmethyl)-N-[4-methyl-3-(4-(pyridin-3-yl)-pyrimidin-2-ylamino)-pheny]-benzamide, or a pharmaceutically acceptable salt thereof.

6. The method according to claim 5 wherein 4-(4-methylpiperazin-1-ylmethyl)-N-[4-methyl-3-(4-(pyridin-3-yl)-pyrimidin-2-ylamino)-pheny]-benzamide is in the form of its monomesylate salt.

* * * * *

UNITED STATES PATENT AND TRADEMARK OFFICE
CERTIFICATE OF CORRECTION

PATENT NO.       : 7,087,608 B2
APPLICATION NO.  : 10/220214
DATED            : August 8, 2006
INVENTOR(S)      : Atkins et al.

It is certified that error appears in the above-identified patent and that said Letters Patent is hereby corrected as shown below:

Column 11
    Claim 5, Line 3, change "bA" to -- IgA --.

Signed and Sealed this

Twentieth Day of March, 2007

JON W. DUDAS
*Director of the United States Patent and Trademark Office*